United States Patent
Lee et al.

(10) Patent No.: US 10,358,403 B2
(45) Date of Patent: Jul. 23, 2019

(54) METHOD FOR RECOVERING PHENOL AND ACETONE FROM CRACKING REACTION PRODUCT OF BISPHENOL-A RESIDUE

(71) Applicant: LG CHEM, LTD., Seoul (KR)

(72) Inventors: Sang-Beom Lee, Daejeon (KR); Joon-Ho Shin, Daejeon (KR); In-Yong Jeong, Daejeon (KR); Jong-Hui Park, Daejeon (KR); Myeong-Yeon Keum, Daejeon (KR); Jeong-Ho Kim, Daejeon (KR); Tae-Ho Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/751,360

(22) PCT Filed: Dec. 7, 2016

(86) PCT No.: PCT/KR2016/014334
§ 371 (c)(1),
(2) Date: Feb. 8, 2018

(87) PCT Pub. No.: WO2017/111357
PCT Pub. Date: Jun. 29, 2017

(65) Prior Publication Data
US 2018/0290954 A1    Oct. 11, 2018

(30) Foreign Application Priority Data

Dec. 23, 2015  (KR) .......... 10-2015-0185426
Oct. 31, 2016  (KR) .......... 10-2016-0143198

(51) Int. Cl.
| C07C 37/08 | (2006.01) |
| C07C 37/74 | (2006.01) |
| C07C 37/68 | (2006.01) |
| C07C 45/53 | (2006.01) |
| C07C 45/78 | (2006.01) |
| C07C 45/82 | (2006.01) |
| C07C 37/52 | (2006.01) |
| C07C 45/51 | (2006.01) |
| C07C 37/72 | (2006.01) |
| C07C 37/86 | (2006.01) |
| C07C 45/80 | (2006.01) |

(52) U.S. Cl.
CPC .............. *C07C 37/08* (2013.01); *C07C 37/52* (2013.01); *C07C 37/68* (2013.01); *C07C 37/72* (2013.01); *C07C 37/74* (2013.01); *C07C 37/86* (2013.01); *C07C 45/512* (2013.01); *C07C 45/517* (2013.01); *C07C 45/53* (2013.01); *C07C 45/78* (2013.01); *C07C 45/80* (2013.01); *C07C 45/82* (2013.01)

(58) Field of Classification Search
None
See application file for complete search history.

(56) References Cited

U.S. PATENT DOCUMENTS

| 8,431,749 B2 | 4/2013 | Palmer et al. |
| 2008/0281129 A1 | 11/2008 | Palmer |
| 2009/0221858 A1 * | 9/2009 | Evitt .................. C07C 2/66 568/724 |
| 2011/0112333 A1 | 5/2011 | Palmer |
| 2012/0310015 A1 | 12/2012 | Palmer et al. |

FOREIGN PATENT DOCUMENTS

| JP | 09-110766 A | | 4/1997 | |
| JP | 09110766 | * | 4/1997 | ............ C07C 39/16 |
| JP | 2009-511474 A | | 3/2009 | |
| JP | 2014-524897 A | | 9/2014 | |
| KR | 10-2010-0017484 A | | 2/2010 | |
| KR | 10-2014-0037843 A | | 3/2014 | |
| KR | 10-2015-0032842 A | | 3/2015 | |

* cited by examiner

*Primary Examiner* — Rosalynd A Keys
(74) *Attorney, Agent, or Firm* — Dentons US LLP

(57) ABSTRACT

Disclosed is a method for recovering phenol and acetone from the cracking reaction product of bisphenol-A residue, by which economic feasibility and efficiency may be improved by utilizing a phenol/acetone purification process used for preparing bisphenol-A.

14 Claims, 1 Drawing Sheet

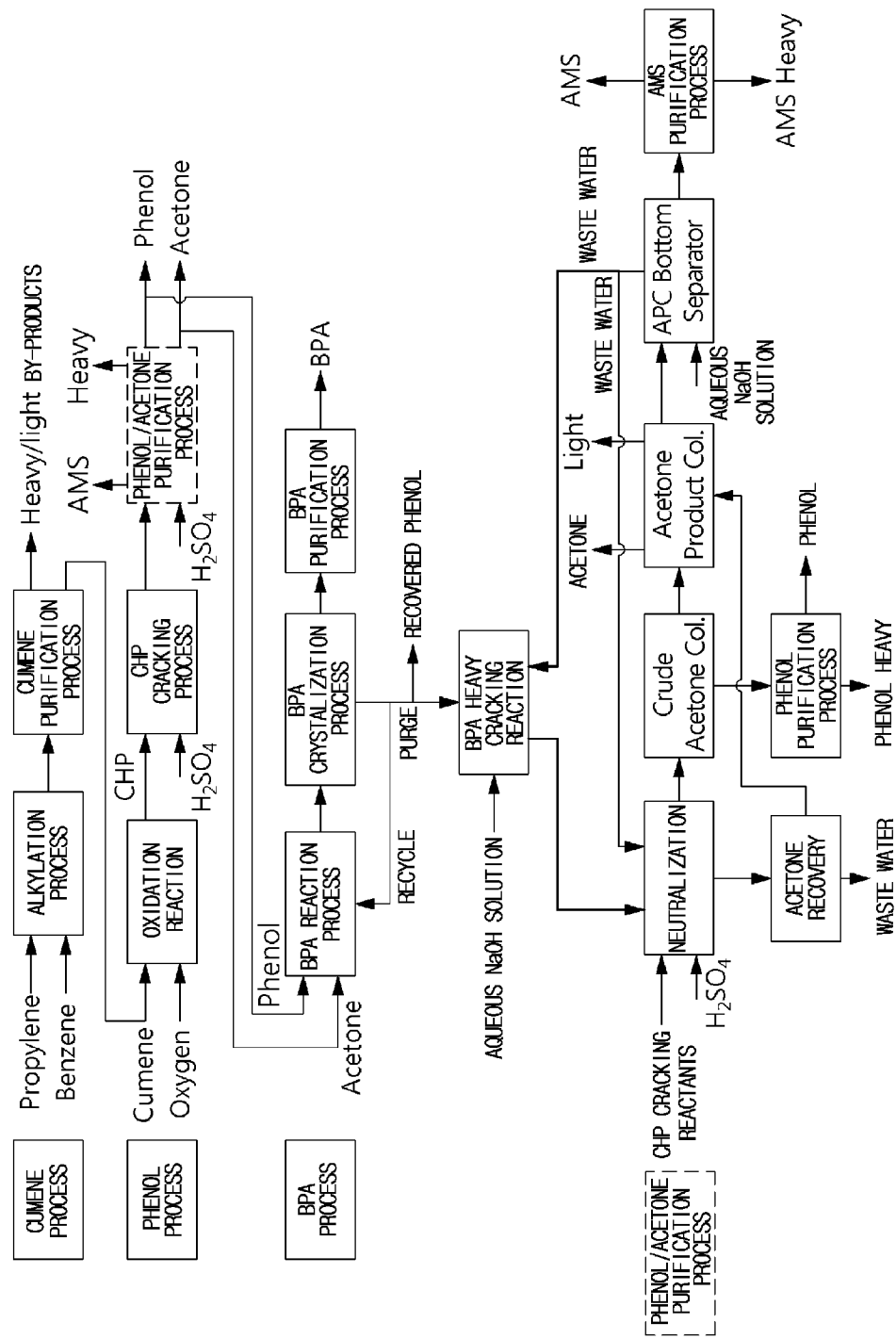

METHOD FOR RECOVERING PHENOL AND ACETONE FROM CRACKING REACTION PRODUCT OF BISPHENOL-A RESIDUE

TECHNICAL FIELD

This application is a National Stage Application of International Application No. PCT/KR2016/014334 filed on Dec. 7, 2016, and claims the benefit of Korean Patent Application No. 10-2015-0185426 filed on Dec. 23, 2015 and Korean Patent Application No. 10-2016-0143198 filed on Oct. 31, 2016, all of which are hereby incorporated by reference in their entirety for all purposes as if fully set forth herein.

The present invention relates to a method for recovering phenol and acetone from a cracking reaction product of bisphenol-A residue, and more particularly, to a method for recovering phenol and acetone from a cracking reaction product of bisphenol-A residue, by which economic feasibility and efficiency may be improved by utilizing a phenol/acetone purification process which is used for preparing bisphenol-A.

BACKGROUND ART

Impurities are accumulated in a process if a production process of bisphenol-A (BPA) from phenol and acetone is used, and in order to prevent this, purge stream is present, and recovering technique of useful components therefrom is disclosed in U.S. Pat. No. 8,431,749 (applicant: Badger, et al.). By using this technique, an excessive amount of an aqueous solution of caustic soda (sodium hydroxide, NaOH) is injected to the purge stream, and phenol and acetone, which are raw materials of BPA may be recovered at a high temperature, with the advantage of a high recovery rate.

When examining the recovery process of phenol and acetone using such technique, the cracking reaction product of bisphenol-A residue is fed to a purification column, acetone is distilled and recovered first, a stream including phenol is transported to a neutralization bath together with an extracting agent, and the stream including phenol and the extracting agent are separated in an upper organic layer and a lower aqueous layer. Then, the extracting agent and phenol in the upper organic layer are respectively recovered via distillation, and remaining phenol in the lower aqueous layer is removed by extraction and discharged to a waste water treatment process.

DISCLOSURE OF THE INVENTION

Technical Problem

As examined above, by the method for recovering phenol and acetone using BPA residue cracking technique, phenol and acetone may be recovered from BPA in high yields, but an additional separation process for recovering phenol and acetone is required, and there are defects such that process equipment becomes excessively complicated and costs increase. In addition, even though a dephenolization process is included in a BPA preparation process, an acetone recovery distillation column and a neutralization bath should be separately installed. In addition, according to the technique of the prior art document, a similar or more amount of water as the amount of a decomposable component in a purge stream is necessary for attaining economical recovery rate, and the increase of waste water arise, and it is apprehended that severe environmental contamination may be generated.

Therefore, an object of the present invention is to provide a method for recovering phenol and acetone from a cracking reaction product of bisphenol-A residue, by which process equipment may be simplified, and investment and operating costs may be saved by utilizing a phenol/acetone purification process which is used for preparing bisphenol-A.

Another object of the present invention is to provide a method for recovering phenol and acetone from a cracking reaction product of bisphenol-A residue, by which costs may be saved and environmental contamination may be decreased by recycling waste water produced during processing and using water which is used during the cracking reaction of bisphenol-A residue.

Technical Solution

In order to accomplish the object, the present invention provides a method for recovering phenol and acetone from a cracking reaction product of bisphenol-A residue, including (a) a step of cracking cumene hydroperoxide which is prepared by an oxidation reaction of cumene, and separating phenol and acetone; (b) a step of separating bisphenol-A which is prepared by reacting the separated phenol and acetone, and cracking a purge stream including unseparated bisphenol-A, or a further concentrated purge stream by discharging and recovering a portion of or entire phenol in an aqueous alkaline solution; and (C) a step of separating phenol and acetone by feeding the reaction product by the cracking reaction to a separation process of phenol and acetone, wherein step (a) and step (C) are conducted at the same time.

Advantageous Effects

By the method for recovering phenol and acetone from a cracking reaction product of bisphenol-A residue according to the present invention, a phenol/acetone purification process used during preparing bisphenol-A is utilized, and process equipment is simplified, and in addition, investment and operating costs may be saved. In addition, waste water produced during processing is reused as water used during cracking reaction, thereby decreasing costs and environmental contamination.

BRIEF DESCRIPTION OF THE DRAWINGS

The Figure is a schematic process diagram for explaining a method for recovering phenol and acetone from a cracking reaction product of bisphenol-A residue according to an embodiment of the present invention.

BEST MODE FOR CARRYING OUT THE INVENTION

Hereinafter, the present invention will be described in more detail referring to attached drawings.

The Figure is a schematic process diagram for explaining a method for recovering phenol and acetone from a cracking reaction product of bisphenol-A residue according to an embodiment of the present invention. When explaining the present invention referring to the Figure, the method for recovering phenol and acetone from a cracking reaction product of bisphenol-A residue according to the present invention includes (a) a step of cracking cumene hydroperoxide which is prepared by an oxidation reaction of cumene, and separating phenol and acetone; (b) a step of separating bisphenol-A which is prepared by reacting the separated phenol and acetone, and cracking a purge stream including unseparated bisphenol-A, or a further concentrated purge stream by discharging and recovering a portion of or entire phenol in an aqueous alkaline solution; and (C) a step of separating phenol and acetone by feeding the reaction product by the cracking reaction to a separation process of phenol and acetone, wherein step (a) and step (C) are conducted at the same time.

The above step (a) is a step using a cumene purification process and a phenol/acetone purification process. First, cumene is prepared via an alkylation reaction of propylene and benzene, and heavy/light by-products are discharged and cumene is purified and separated via a purification process. Then, the purified cumene is undergone an oxidation reaction to prepare cumene hydroperoxide (CHP), and the cumene hydroperoxide (CHP) is undergone a cracking reaction in the presence of a common acid catalyst such as sulfuric acid ($H_2SO_4$) to produce phenol, acetone, α-methyl styrene (AMS) and heavy by-products, and to discharge α-methyl styrene (AMS) and heavy by-products and to purify and separate phenol and acetone via a purification reaction.

Subsequently, the above step (b) is a step using a bisphenol-A purification process. First, the purified and separated phenol and acetone are reacted to prepare bisphenol-A (BPA), more accurately, crude bisphenol-A, and then, bisphenol-A with improved purity is prepared via a crystallization process. The bisphenol-A thus prepared undergoes two routes, and according to one route, bisphenol-A of a para, para type with a purity of 99% or more is separated via a BPA purification process and productized, and according to the other route, the bisphenol-A is recycled together with heavy by-products and phenol produced during preparing bisphenol-A to a reactor, or becomes a purge stream to be cracked in an aqueous alkaline solution. Meanwhile, phenol constituting the purge stream may be unreacted phenol and phenol used for washing during a BPA crystallization process, that is, cleaning phenol. In addition, the concentrated purge stream is obtained by excluding a portion of or entire phenol by discharging and recovering thereof via distillation.

Here, the purge stream including bisphenol-A may include 5 to 20 wt % of bisphenol-A, 60 to 90 wt % of phenol, and 3 to 15 wt % of an isomer and heavy by-products. The concentrated purge stream includes 40 to 60 wt % of bisphenol-A, 0 to 15 wt % of phenol, and 35 to 60 wt % of an isomer and heavy by-products. The purge streams are cracked in an excessive amount of an aqueous alkaline solution having basic properties such as NaOH, KOH and LiOH. In this case, the feed amount of alkali may be from 2 to 40 parts by weight, preferably, from 5 to 30 parts by weight based on 100 parts by weight of the purge stream. In addition, in the above step (b), the reaction of phenol and acetone is performed at 40 to 150° C., preferably, from 50 to 100° C., and the cracking reaction may be performed at 150 to 300° C., preferably, from 200 to 280° C.

Finally, the above step (C) is a step for reusing a phenol/acetone purification process used in the above step (a), and for recovering phenol and acetone, and is a separation method for easy liquid-liquid separation by neutralization, because the product by the cracking reaction of the above step (b) includes an excessive amount of an aqueous alkaline solution. As described above, since step (C) reuses the phenol/acetone purification process used in the above step (a), in a neutralization bath in which a neutralization reaction is performed, the cumene hydroperoxide cracking product of the above step (a) may be fed as well as the cracking reaction product of bisphenol-A residue of the above step (b).

In this case, the cumene hydroperoxide cracking product and the cracking reaction product of bisphenol-A residue may be controlled in various ratios according to the need of a user, but preferably, are fed to a neutralization bath in a ratio of 75:25 to 99:1%. Meanwhile, in the cracking reaction product of bisphenol-A residue, from 5 to 50 wt % of phenol and acetone, from 2 to 15 wt % of an alkali metal hydroxide, from 30 to 90 wt % of water, and from 3 to 15 wt % of remaining by-products are included. In addition, the neutralization reaction may be performed at 20 to 100° C., preferably, from 30 to 70° C.

The above step (a) and step (C) are performed simultaneously, and in this case, the separation of phenol/acetone is performed via (i) a step of injecting a common acid such as sulfuric acid ($H_2SO_4$) to the cumene hydroperoxide product and the cracking reaction product of bisphenol-A residue to neutralize and to separate a stream including crude acetone and phenol and an aqueous layer including a portion of acetone; (ii) a step of recovering by separating and purifying phenol from the stream including crude acetone and phenol; (iii) a step of recovering acetone by mixing the stream including the crude acetone from which phenol is removed and acetone recovered from the aqueous layer, and distilling, discharging hydrocarbons having a lower boiling point than acetone as light materials, and separating hydrocarbons having a higher boiling point than acetone including a portion of water (at the bottom part of a column); and (iv) a step of layer separating the hydrocarbons having a higher boiling point than acetone using a common basic material such as caustic soda and separating waste water and a stream including alpha methyl styrene (AMS), and recycling to the cracking step of bisphenol-A residue or the neutralization step, or discharging the waste water.

If the stream including crude acetone and phenol, which are separated in the above step (i) is fed to a crude acetone column, phenol and heavy by-products, which have a relatively high boiling point, are separated at the bottom part of the column and phenol is recovered via a phenol purification process. The crude acetone which has a relatively lower boiling point than phenol is transported to an acetone product column. The neutralization bath is a layer separator in which a liquid-liquid separation is performed by neutralization. Components including water and by-products included in the aqueous layer are discharged as waste water, acetone included in the aqueous layer is separated and transported together with the crude acetone to the acetone product column and distilled to recover acetone. In this case, light by-products are also separated apart and discharged. Meanwhile, the amount of acetone recovered from the cracking reaction product of bisphenol-A residue relative to the amount of acetone used for preparing bisphenol-A is from 1 to 7%.

Meanwhile, the remaining hydrocarbons which have a higher boiling point than acetone include phenol and are separated in layers using a common basic material such as caustic soda, thereby being separated into waste water including a portion of hydrocarbons and a stream including α-methyl styrene (AMS). The waste water is recycled to the cracking step of bisphenol-A residue or the neutralization step, and the stream including α-methyl styrene is separated and purified to recover α-methyl styrene. That is, hydrocarbons including water and positioned at the bottom part of the acetone product column is a mixture of α-methyl styrene produced by the cracking reaction of cumene hydroperoxide (CHP) and a phenyl group-containing material such as unreacted cumene. If the mixture is fed to an acetone product column (APC) bottom separator with an aqueous alkaline solution, separation in an upper layer is attained under the aqueous alkaline solution, and an α-methyl styrene separation and purification process is performed. A separated lower aqueous layer contains phenolate and is recycled to the cracking step of bisphenol-A residue or the neutralization step as waste water and reused.

The aqueous alkaline solution used herein is also an aqueous solution including an alkali metal hydroxide selected from the group consisting of NaOH, KOH, and LiOH. Phenol in an aqueous MOH (where M means an alkali metal) solution is ionized to form phenolate, and the phenolate is transformed into phenol via the exchange of metal ions with hydrogen ions of an acid such as sulfuric acid. In other words, phenol in the hydrocarbons of the above step (iii) is ionized in an aqueous alkaline solution to form phenolate, and then is recycled to the cracking step of bisphenol-A residue or the neutralization step as waste water and reused.

Such reused waste water, namely waste water discharged during separating phenol and acetone in the above steps (a) and (c) is fed to the cracking step of bisphenol-A residue (b) or the neutralization step and reused. The waste water including phenol is preferably fed to the neutralization step so as to easily recover phenol in a phenol/acetone purification process, but a small amount of hydrocarbons (phenol, α-methyl styrene, unreacted cumene, etc.) may be included in the waste water reused in the cracking reaction of bisphenol-A residue. The amount of waste water used in the cracking step of bisphenol-A residue and the amount of waste water used in the neutralization step may be controlled in various ratios according to the need of a user, but may preferably be fed in a ratio of 20-100%:80-0%.

Meanwhile, α-methyl styrene among components transported to the acetone product column (APC) bottom separator via the bottom part of the acetone product column may be included in the waste water in a small amount, but most of them is transported to an α-methyl styrene purification process and separated from heavy by-products and discharged.

As described above, the method for recovering phenol and acetone from the cracking reaction product of bisphenol-A residue according to the present invention utilizes a phenol/acetone purification process used for preparing bisphenol-A in order to recover phenol and acetone from the cracking reaction product of bisphenol-A residue, and the recovery rate of phenol and acetone is excellent and is enough to be the same as the recovery rate of phenol/acetone in U.S. Pat. No. 8,431,749 (recover of phenol and acetone from a bisphenol-A stream), in which a separate separation process is required to be provided to recover phenol and acetone. Like this, the present invention has excellent recovery rate of phenol and acetone even though using a preceding purification process, and thus, process equipment may be simplified and consequential investment and operating costs may be saved. In addition, by recycling waste water produced during processing as water used during the cracking step of bisphenol-A residue, costs may be saved, and environmental contamination may be decreased.

Mode For Carrying Out the Invention

Hereinafter, preferred embodiments will be suggested to assist the understanding of the present invention, but the following embodiments are only for illustration of the inventive concept, and various changes and modifications can be made by one ordinary skilled in the art within the technical spirit and scope of the present invention, and such changes and modifications are absolutely included in the claims attached herein.

EXAMPLE 1

Recovery of Phenol and Acetone Using Waste Water

When explaining referring to the Figure, first, 1.90 g of sodium hydroxide (NaOH) was dissolved in 16.86 g of waste water came from an APC bottom separator, and then, 12.50 g of remaining material with a high boil point (BPA heavies) having the composition shown in Table 1 below, recovered from the purge stream of a BPA process by distillation, and 18.76 g of the aqueous solution of sodium hydroxide waste water were fed to a reactor of a SUS316 (Japanese industrial standards, JIS) or a STS316 (Korean industrial standards, KS) material, followed by elevating the temperature to 250° C. and maintaining for 2 hours. Such a cracking reaction process was performed twice by the same manner, and the compositions of BPA heavies after completing the reaction are shown in Table 2 below. Meanwhile, in Tables 1 and 2, the reason why the total amount does not reach 100 wt % is because of errors which may be shown during practical instrumental analysis. In the composition of BPA heavies shown in Table 1, a heavy value may be increased, and in the compositions of BPA heavies shown in Table 2, water (H2O) and sodium hydroxide (NaOH) may be additionally included.

COMPARATIVE EXAMPLE 1

Recovery of Phenol and Acetone Using Distilled Water

The same procedure described in Example 1 was performed twice except for using 1.97 g of sodium hydroxide (NaOH) instead of 0.90 g, using distilled water instead of 17.54 g of waste water, and using 12.99 g of remaining material with a high boiling point (BPA heavies) instead of 12.50 g. The compositions of BPA heavies after completing the reaction are shown in Table 2 below.

TABLE 1

|  | Phenol | Isopropenyl phenol | p,p-BPA | o,p-BPA | BPX | heavy |
|---|---|---|---|---|---|---|
| Amount (wt %) | 7.66 | 0.093 | 42.56 | 18.14 | 6.85 | 24.69 |

TABLE 2

|  |  | acetone | phenol | Isopropenyl phenol | p,p-BPA | o,p-BPA | BPX | heavy |
|---|---|---|---|---|---|---|---|---|
| Example 1 | Once (wt %) | 7.12 | 26.88 | 0.005 | 1.71 | 0.43 | 0.13 | 9.41 |
|  | Twice (wt %) | 7.16 | 25.45 | 0.004 | 1.41 | 0.38 | 0.04 | 7.25 |

TABLE 2-continued

|  |  | acetone | phenol | Isopropenyl phenol | p,p-BPA | o,p-BPA | BPX | heavy |
|---|---|---|---|---|---|---|---|---|
| Comparative Example 1 | Once (wt %) | 7.00 | 26.86 | 0.008 | 1.93 | 0.47 | 0.05 | 8.50 |
|  | Twice (wt %) | 7.40 | 26.27 | 0.002 | 2.18 | 0.67 | 0.13 | 9.28 |

EXAMPLE 1 and COMPARATIVE EXAMPLE 1

Evaluation of Recovery Rate of Phenol and Acetone

In Comparative Example 1 using distilled water, the recovery rate of phenol and acetone per unit mass of BPA heavies (weight of (phenol+acetone)/weight of BPA heavies) was 78% (once) and 75% (twice). In addition, even though a portion of the distilled water used was consumed in the reaction, most of the distilled water was required to be treated as waste water. Meanwhile, in Example 1 recycled waste water, even though waste water produced during processing was used, the equivalent level of recovery rate of phenol and acetone per unit mass of BPA heavies (weight of (phenol+acetone)/weight of BPA heavies) to Comparative Example 1 was shown. In addition, since waste water produced during a conventional process was recycled, separate waste was not additionally produced, but a portion of the waste water was rather used for the conversion into phenol and acetone, thereby securing the reduction of the amount of waste water.

EXAMPLE 2

Separation into Layers in Neutralization Bath

When explaining referring to the Figure, 20 g of components in an aqueous layer discharged from a neutralization bath was injected to a neutralization bath of 50° C. for the sufficient separation into layers, and then, 14 g of a reaction product produced by the cracking reaction in Example 1 was additionally fed to the neutralization bath, followed by stirring and adjusting pH to a level of 6.6 using sulfuric acid (H2SO4). Within a few minutes after standing, separation into layers was attained, and the amount of components in each layer was analyzed.

EXAMPLE 3

Separation into Layers in Neutralization Bath

Separation into layers in a neutralization bath was attained by performing the same procedure described in Example 2 except for additionally feeding 1 g of a mixture solution of cumene and α-methyl styrene (AMS) to copy the conventional neutralization bath, and the amount of components in each layer was analyzed.

EXAMPLES 2 and 3

Performance Evaluation of Separation into Layers in Neutralization Bath

The separation into layers in a neutralization bath of both Examples 2 and 3 was attained in a short time. In Example 2, the amount of water ($H_2O$) in an organic layer was measured as 12 wt %, and the amount of an organic material in an aqueous layer was measured as 1 wt %. In Example 3, the amount of water ($H_2O$) in an organic layer was measured as 8.5 wt %, and the amount of an organic material in an aqueous layer was measured as 1.2 wt %. Both Examples 2 and 3 show excellent layer separation performance.

As secured from the examples described above, if the cracking reaction of BPA heavies is performed using not distilled water but waste water produced during processing, equivalent reactivity may be attained, and additional production of waste water may be prevented (Example 1), and in addition, by using the conventional separation process, investment costs and operation costs may be saved (Example 2 and 3).

The invention claimed is:
1. A method for recovering phenol and acetone from a cracking reaction product of bisphenol-A residue, the method comprising:
   (A) a step of cracking cumene hydroperoxide which is prepared by an oxidation reaction of cumene, and producing phenol and acetone;
   (A-1) a step of separating phenol and acetone;
   (B) a step of separating bisphenol-A which is prepared by reacting the separated phenol and acetone, and cracking a bisphenol-A residue in a purge stream comprising unseparated bisphenol-A in an aqueous alkaline solution; and
   (C) a step of feeding the reaction product by the cracking reaction of the bisphenol-A residue to the step (A-1).
2. The method for recovering phenol and acetone according to claim 1, wherein the bisphenol-A residue in the purge stream is cracked immediately, or the bisphenol A residue is cracked after the purge stream is further concentrated by discharging and recovering a portion, or entirety, of phenol.
3. The method for recovering phenol and acetone according to claim 1, wherein the separation of phenol and acetone in step (A-1) and step (C) is conducted by the following:
   (i) a step of injecting an acid to the cumene hydroperoxide cracking product of step (A-1) and the cracking reaction product of bisphenol-A residue of step (B) to neutralize and to separate a stream including crude acetone and phenol and an aqueous layer including a portion of acetone;
   (ii) a step of recovering by separating and purifying phenol from the stream including crude acetone and phenol;
   (iii) a step of recovering acetone by mixing the stream including the crude acetone from which phenol is removed and acetone recovered from the aqueous layer and distilling, discharging hydrocarbons having a lower boiling point than acetone as light materials, and separating hydrocarbons having a higher boiling point than acetone including water; and
   (iv) a step of layer separating the hydrocarbons having a higher boiling point than acetone using a basic material and separating waste water and a stream including alpha methyl styrene (AMS), and reusing the waste water by feeding the waste water to the step (i) or the step (B).

4. The method for recovering phenol and acetone according to claim 3, wherein the hydrocarbon in step (iii) comprises phenol.

5. The method for recovering phenol and acetone according to claim 3, wherein the phenol in the hydrocarbon in step (iii) is ionized in an aqueous alkaline solution to form phenolate, and recycled to the step (i) or the step (b) as waste water and reused.

6. The method for recovering phenol and acetone according to claim 1, wherein the aqueous alkaline solution is an aqueous solution including an alkali metal hydroxide selected from the group consisting of NaOH, KOH and LiOH.

7. The method for recovering phenol and acetone according to claim 3, wherein the cumene hydroperoxide cracking product and the cracking reaction product of bisphenol-A residue are fed to the neutralization bath in a ratio of 75:25-99:1%, and neutralized.

8. The method for recovering phenol and acetone according to claim 1, wherein an amount of acetone recovered from the cracking reaction product of bisphenol-A residue with respect to an amount of acetone used for preparing bisphenol-A is from 1 to 7%.

9. The method for recovering phenol and acetone according to claim 1, wherein a feed amount of alkali used in step (B) is from 2 to 40 parts by weight based on 100 parts by weight of the purge stream.

10. The method for recovering phenol and acetone according to claim 3, wherein an amount of waste water used in the cracking step of step (B) and an amount of waste water used in the neutralization step of step (i) are fed in a ratio of 20-100%:80-0%.

11. The method for recovering phenol and acetone according to claim 1, wherein the reaction of phenol and acetone to prepare bisphenol-A of the step (B) is performed at 40 to 150° C.

12. The method for recovering phenol and acetone according to claim 1, wherein the cracking reaction of the bisphenol-A of the step (B) is performed at 150 to 300° C.

13. The method for recovering phenol and acetone according to claim 3, wherein the neutralization reaction of the step (i) is performed at 20 to 100° C.

14. The method for recovering phenol and acetone according to claim 5, wherein the aqueous alkaline solution is an aqueous solution including an alkali metal hydroxide selected from the group consisting of NaOH, KOH and LiOH.

* * * * *